United States Patent [19]

Schubart

[11] Patent Number: 5,210,285

[45] Date of Patent: May 11, 1993

[54] PROCESS FOR THE PREPARATION OF BETA-HALOGENO-TERT.-ALKYL ISOCYANATES

[75] Inventor: Rüdiger Schubart, Bergisch-Gladbach, Fed. Rep. of Germany

[73] Assignee: Bayer Aktiengesellschaft, Leverkusen, Fed. Rep. of Germany

[21] Appl. No.: 862,042

[22] Filed: Apr. 2, 1992

[30] Foreign Application Priority Data

Apr. 12, 1991 [DE] Fed. Rep. of Germany ....... 4111905

[51] Int. Cl.$^5$ .............................................. C07C 263/16
[52] U.S. Cl. .................................... 560/349; 521/155; 560/356
[58] Field of Search ........................................ 560/349

[56] References Cited

U.S. PATENT DOCUMENTS

| | | | |
|---|---|---|---|
| 3,277,137 | 10/1966 | Powers | 560/349 X |
| 3,281,448 | 10/1966 | Start | 560/349 |
| 3,468,923 | 9/1969 | Koenig et al. | 560/349 |
| 3,536,360 | 10/1970 | Holtschmidt et al. | 560/349 |
| 4,344,891 | 8/1982 | Koenig et al. | 560/349 X |

FOREIGN PATENT DOCUMENTS

| | | |
|---|---|---|
| 0025907 | 4/1981 | European Pat. Off. |
| 1418666 | 11/1968 | Fed. Rep. of Germany |
| 1353680 | 5/1974 | United Kingdom |

Primary Examiner—José G. Dees
Assistant Examiner—Vera C. Clarke
Attorney, Agent, or Firm—Sprung Horn Kramer & Woods

[57] ABSTRACT

The invention relates to a new process for the preparation of known β-halogeno-tert.-alkyl isocyanates of the formula

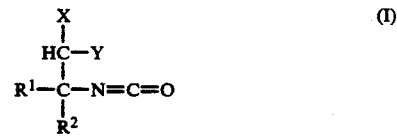

in which
X represents chlorine,
Y represents hydrogen or chlorine,
R$^1$ represents in each case straight-chain or branched alkyl or halogeno alkyl and
R$^2$ represents in each case straight-chain or branched alkyl or halogeno alkyl or optionally halogen-and/or trifluoromethyl-substituted phenyl, where tert.-alkyl isocyanates of the formula (II)

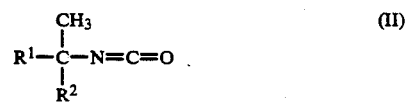

are reacted with chlorine, optionally under irradiation or in the presence of catalysts, in a suitable apparatus.

9 Claims, No Drawings

PROCESS FOR THE PREPARATION OF BETA-HALOGENO-TERT.-ALKYL ISOCYANATES

The invention relates to a new process for the preparation of known β-halogeno-tert.-alkyl isocyanates, which can be used as intermediates for the synthesis of rubber additives or of biologically active compounds, such as for example herbicides (cf. e.g. EP-A 294 666).

It is already known that β-monochloro-tert.-alkyl isocyanates are obtained when β-hydroxy-tert.-alkylamines are first hydrochlorinated using thionyl chloride and then the corresponding chloro-amine-hydrochloride is converted to the isocyanate using phosgene (cf. DE-OS (German Published Specification) 2 045 906).

The poor yields of the chlorinated tert.-alkyl isocyanates are a disadvantage of this process.

The reaction of methyl isocyanate with chlorine under irradiation is further already known (cf. Houben-Weyl volume E4, page 1171). However, in this way, the polychlorinated chlorocarbonyl isocyanide dichloride is obtained.

It has now been found that β-halogeno-tert.-alkyl isocyanates of the formula (I)

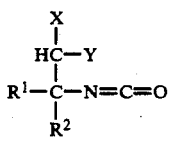

(I)

in which
X represents chlorine,
Y represents hydrogen or chlorine,
$R^1$ represents in each case straight-chain or branched alkyl or halogeno alkyl and
$R^2$ represents in each case straight-chain or branched alkyl or halogeno alkyl or optionally halogen- and/or trifluoromethyl-substituted phenyl,
are obtained in good yields and high purity, when tert.-alkyl isocyanates of the formula (II)

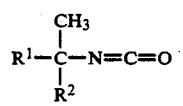

(II)

in which
$R^1$ and $R^2$ have the definition given above,
are reacted with elemental chlorine, optionally under irradiation or in the presence of catalysts, in a suitable apparatus according to the invention (see in this regard for example DE 27 16 896), for which 2 process variants are available, namely a batch halogenation and a continuous halogenation.

It is extremely surprising that the chlorination gives the desired β-halogeno-tert.-alkyl isocyanates of the formula (I) in good yields. Since HCl is liberated in the reaction, it was rather to be expected that the HCl would add to the isocyanate (cf. Houben Weyl, volume E4, page 57–58), and that the yield would thereby be markedly reduced. Moreover, during the reaction of isocyanates with halogen under irradiation, fragmentations (cf. Houben Weyl 4/5b Photochemie I and II, 891–892) or elimination of the tert.-alkyl moiety in the form of tert.-alkyl chloride (cf. Houben Weyl vol. E4 p. 63) had to be expected.

With the aid of the process according to the invention, compounds of the formula (I) are preferably obtained in which $R^1$ represents methyl, ethyl, n- or iso-propyl, n-, iso-, sec.- or tert.-butyl, $R^2$ represents methyl, ethyl, n- or iso-propyl, n-, iso-, sec.- or tert.-butyl, or represents optionally mono- to trisubstituted phenyl, identically or differently substituted by fluorine, chlorine, bromine and/or trifluoromethyl, especially preferably $R^1$ represents methyl or ethyl and $R^2$ represents methyl, ethyl or phenyl, in particular methyl.

Very especially preferably, the compounds of the formula (I) in which X represents chlorine and Y represents hydrogen, i.e. β-monochlorinated tert.-alkyl isocyanates, may be prepared by the process according to the invention.

The process according to the invention can, in the case of the use of tert.-butyl isocyanate, be described by the following equation:

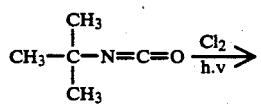

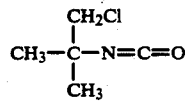

The process according to the invention can also be carried out in the presence of diluents. All diluents normal for such halogenation reactions can be used, such as for example dichloromethane, chloroform or tetrachloromethane. Tetrachloromethane is preferably used.

The process according to the invention is preferably carried out without addition of diluents.

The direct halogenation of tert.-alkyl isocyanates of the formula (II) can be carried out optionally under irradiation or by addition of suitable catalysts.

The irradiation can be carried out for example using a water-cooled high-pressure mercury vapour lamp, it being possible for the halogenation lamp to be either an immersion lamp or mounted externally. In mounting the lamp, care must be taken that as much light as possible reaches the halogenation zone. All high-pressure mercury vapour lamps normally used for such halogenations may be used for the process according to the invention. Naturally, other lamps suitable for such halogenations may also be used.

The catalysts used are preferably peroxides, such as for example cumyl peroxide or benzoyl peroxide, or azo compounds such as for example azoisobutyronitrile (AIBN).

The reaction temperatures can be varied in a wide range in carrying out the process according to the invention. In general temperatures between 40° C. and 120° C. are employed, preferably between 60° C. and 110° C., especially preferably between 85° C. and 100° C. In particular, the temperatures employed are in the region of the boiling point of the tert.-alkyl isocyanate to be chlorinated or of the diluent.

The process according to the invention can be carried out in two different variants: as a batch halogenation (variant 1) or in the form of a continuous halogenation (variant 2).

For carrying out variant 1 of the process (batch halogenation), when the monohalogenated compounds of the formula (I) (i.e. X=chlorine and Y=hydrogen) are to be obtained, then per mole of tert.-alkyl isocyanate of the formula (II), equivalent amounts or a slight excess of halogen are generally used. When the dihalogenated compounds of the formula (I) are to be prepared, then an excess of halogen, preferably up to 2.5 mol, especially preferably up to 2.1 mol per mole of tert.-alkyl isocyanate of the formula (II), is used.

In an apparatus suitable for variant 2, which for example consists of a distillation flask, a packed column, a condenser and the chlorination device, the starting material is first evaporated. This passes through the column to the condenser, and condenses there. The condensed starting material can now, either in whole or in part, be passed through the chlorination zone, which is simultaneously illuminated and supplied with chlorine. The reaction mixture that forms in this chlorination zone, consisting of starting material and product of the formula (I), is now passed to the separation column for separation into the components. A correspondingly suitable apparatus is for example described in DE 27 16 896. However, in principle other types of apparatus are also usable for this circulatory process.

For carrying out variant 2 of the process (continuous halogenation), when the monohalogenated compounds of the formula (I) are to be obtained, then equivalent amounts or a slight excess of halogen is generally used per mole of tert.-alkyl isocyanate of the formula (II). When the dihalogenated compounds of the formula (I) are to be prepared, then, generally, equivalent amounts or an excess of halogen, preferably up to 2.25 mol, especially preferably up to 2.05 mol, is used per mole of tert.-alkyl isocyanate. It is most practical to use a small excess of halogen in the continuous halogenation for preparation of the dihalogenated compounds.

If the process is carried out in the presence of catalysts, then, per mole of tert.-alkyl isocyanate of the formula (II), in general 0.001 to 1.5 mol%, preferably 0.02 to 1 mol% and especially preferably 0.1 to 0.5 mol% of catalyst is used.

The batch halogenation is carried out in such a way that undiluted chlorine is passed into boiling undiluted, or optionally diluted, tert.-alkyl isocyanate of the formula (II).

The halogenation reaction can be allowed to proceed to almost complete conversion, as a rule up to 95%, or the halogenation reaction is interrupted at an earlier conversion time point, e.g. at about 60% conversion. Conversion is defined in this context as 100% starting material minus the starting material still present. The reaction mixture is then fractionated in order to recover non-halogenated starting material, which is returned to the reaction.

In the batch halogenation the reaction is generally interrupted at a conversion of 40 to 80%, preferably 45–65%, especially preferably 50–55%.

The advantage of proceeding in this manner is that the proportion of by-products and thus the loss of material (i.e. loss of starting material of the formula (II)) is markedly lower.

In this way the yield of β-halogeno-tert.-alkyl isocyanate from a given quantity of tert.-alkyl isocyanate can be markedly improved.

In the continuous process, tert.-butyl isocyanate and chlorine are feed separately to a reaction zone, preferably under irradiation or with addition of a catalyst, and the reaction mixture, which contains starting material of the formula (II) and product of the formula (I), is continuously removed from the halogenation zone. This mixture is passed to a column for fractionation, and non-halogenated isocyanate, i.e. starting material of the formula (II), is immediately separated off, and with fresh tert.-alkyl isocyanate returned to the halogenation zone. The halogenated tert.-alkyl isocyanate, i.e. compounds of the formula (I), is separated off at the bottom of the apparatus and if of sufficient purity is used. directly for further reactions, or continuously removed from the apparatus and subjected to fine fractionation.

This procedure gives a continuous process in which reaction mixture is continuously removed and fresh starting material and chlorine are continuously supplied.

The mixing of the halogen in the reaction zone which is optionally flooded can be achieved e.g. by stirring, by the flow of the reaction partners during addition in a Venturi tube, or a combination of these possibilities as well as with the aid of other possible suitable devices.

In this manner mono- or dihalogenated compounds of the formula (I) are obtained as desired in high yield and purity, and the formation of by-products is restricted. With a relatively small apparatus, large amounts of the desired product can be prepared by the continuous procedure per unit of time.

In the continuous reaction procedure, the chlorination of the tert.-butyl isocyanate passing through the chlorination zone is generally carried out to a conversion between 0.1 and 30%, preferably between 2 and 20%, especially preferably between 5 and 15%, and the resulting product is continuously separated, so that, overall, chlorine and tert.-alkyl isocyanate are supplied to the apparatus and chlorinated tert.-alkyl isocyanate practically free from starting material is removed from the apparatus.

With the batch halogenation as well as the continuous halogenation, the reaction can be interrupted and the process resumed after some time. The reaction mixture can also be set aside, and only further processed after some time.

In principle, both reaction variants are also applicable to the bromination of tert.-alkyl isocyanates.

The process according to the invention is illustrated by the following examples.

EXAMPLE 1

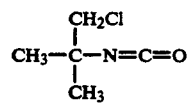

Batch Halogenation 812 g of tert.-butyl isocyanate are initially introduced, and are chlorinated with stirring by direct introduction of undiluted chlorine at 85° to 100° C. under irradiation by a (water-cooled) high-pressure Hg vapour immersion lamp. Samples are taken and the course of chlorination is followed by gas chromatography (GC). After a conversion of 95%, the reaction is terminated. 1225 g of crude product are obtained, which is fractionated on a 20 cm packed column (containing 3 mm glass Raschig rings).

The composition of the chlorination mixture immediately after the end of chlorination is as follows (in % by area):

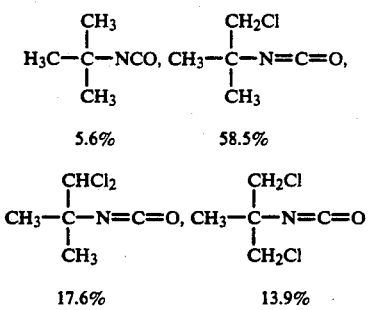

| | |
|---|---|
| $\underset{\underset{CH_3}{\overset{CH_3}{|}}}{H_3C-\overset{|}{C}-NCO}$ | $\underset{\underset{CH_3}{\overset{CH_2Cl}{|}}}{CH_3-\overset{|}{C}-N=C=O}$ |
| 5.6% | 58.5% |
| $\underset{\underset{CH_3}{\overset{CHCl_2}{|}}}{CH_3-\overset{|}{C}-N=C=O}$ | $\underset{\underset{CH_2Cl}{\overset{CH_2Cl}{|}}}{CH_3-\overset{|}{C}-N=C=O}$ |
| 17.6% | 13.9% |

The following are obtained:

1st fraction

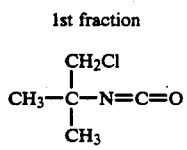

$$CH_3-\underset{\underset{CH_3}{|}}{\overset{\overset{CH_2Cl}{|}}{C}}-N=C=O$$

desired product
yield: 627 g (60.7% of theory) relative to isocyanate used minus 5%, since chlorination was only carried out to 95% conversion.
boiling point: 44.5° C./15 mbar
purity: 98.5% (GC)

2nd fraction:

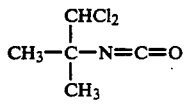

$$CH_3-\underset{\underset{CH_3}{|}}{\overset{\overset{CHCl_2}{|}}{C}}-N=C=O$$

yield: 177.5 g
boiling point: 61.5°-62° C./19 mbar
purity: 96.8% (GC)

3rd fraction:

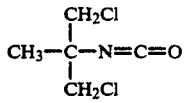

$$CH_3-\underset{\underset{CH_2Cl}{|}}{\overset{\overset{CH_2Cl}{|}}{C}}-N=C=O$$

yield: 80.5 g
boiling point: 65° C./18 mbar
purity: 96.3% (GC)

EXAMPLE 2

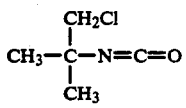

$$CH_3-\underset{\underset{CH_3}{|}}{\overset{\overset{CH_2Cl}{|}}{C}}-N=C=O$$

Continuous Process

In an apparatus suitable for such a continuous chlorination, at least 800 g of tert.-butyl isocyanate are initially introduced and are slowly chlorinated as described above by partial chlorination of the starting material that is in circulation. When the conversion has reached approximately 95%, the reaction can be terminated, or tert.-butyl isocyanate and chlorine at a ratio of 1:1.05 can be continuously supplied to the apparatus and upstream of the chlorination zone respectively and chlorinated product containing virtually no starting material can be removed from the apparatus.

800 g of tert.-butyl isocyanate, at a conversion rate of 95%, give up to 1027 g of monochloro-tert.-butyl isocyanate (boiling point 44.5° C. at 15 mbar, $n_D^{20}$ 1.4355) having a purity of up to 98.2%, where the crude composition consisted of the following products (in % by area):

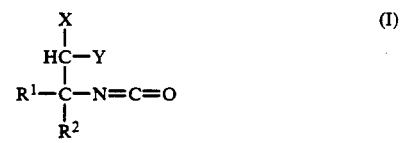

| | |
|---|---|
| $\underset{\underset{CH_3}{\overset{CH_3}{|}}}{H_3C-\overset{|}{C}-NCO}$ | $\underset{\underset{CH_3}{\overset{CHCl_2}{|}}}{H_3C-\overset{|}{C}-NCO}$ |
| 4.7% | 2,2% |

| | |
|---|---|
| $\underset{\underset{CH_2Cl}{\overset{CH_2Cl}{|}}}{H_3C-\overset{|}{C}-NCO}$ | $\underset{\underset{CH_3}{\overset{CH_2Cl}{|}}}{H_3C-\overset{|}{\phantom{C}}-NCO}$ |
| 2.4% | 88.6% |

This corresponds to a theoretical yield of 89.7% of monochloro-tert.-butyl isocyanate, where 4.7% of the tert.-butyl isocyanate was recovered, and so excluded from the calculation.

It will be understood that the specification and examples are illustrative but not limitative of the present invention and that other embodiments within the spirit and scope of the invention will suggest themselves to those skilled in the art.

What is claimed is:

1. A process for the preparation of β-halogeno-tert.-alkyl isocyanates of the formula (I)

$$\underset{R^2}{\overset{X}{\underset{|}{R^1-\overset{|}{C}-N=C=O}}}\overset{HC-Y}{\phantom{R^1-C-N=C=O}} \quad (I)$$

in which
  x represents chlorine,
  Y represents hydrogen or chlorine,
  $R^1$ represents in each case straight-chain or branched alkyl or halogeno alkyl and
  $R^2$ represents in each case straight-chain or branched alkyl or halogeno alkyl or optionally halogen- and-/or trifluoromethyl-substituted phenyl,
which comprises reacting a tert.-alkyl isocyanate of the formula (II)

$$\underset{R^2}{\overset{CH_3}{\underset{|}{R^1-\overset{|}{C}-N=C=O}}} \quad (II)$$

in which
  $R^1$ and $R^2$ have the definition given above, with elemental chlorine.

2. A process according to claim 1, characterised in that $R^1$ represents methyl, ethyl, n- or iso-propyl, n-, iso, sec.-, tert.-butyl and their monohalogenated derivatives, and $R^2$ represents methyl, ethyl, n- or iso-propyl, n-, iso-, sec.- or tert.-butyl and their monohalogenated derivatives or represents optionally mono- to trisubstituted phenyl, identically or differently substituted by fluorine, chlorine, bromine and/or trifluoromethyl.

3. A process according to claim 1, characterised in that $R^1$ represents methyl or ethyl and $R^2$ represents methyl, ethyl or phenyl.

4. The process according to claim 1, wherein the reaction is carried in the presence of peroxides or azo compounds that are used as catalysts.

5. The process according to claim 1, wherein the reaction is carried out as a batch halogenation.

6. The process according to claim 5, wherein the reaction is interrupted at a conversion of 40–80%.

7. The process according to claim 1, wherein the reaction is carried out as a continuous halogenation.

8. The process according to claim 7, wherein the chlorination is carried out to a conversion of between 0.1 and 30% of the tert.-alkyl isocyanante passing through the chlorination zone.

9. The process according to claim wherein the reaction is carried out under irradiation.

* * * * *

UNITED STATES PATENT AND TRADEMARK OFFICE
CERTIFICATE OF CORRECTION

PATENT NO. : 5,210,285
DATED : May 11, 1993
INVENTOR(S) : Rudiger Schubart It is certified that error appears in the above-identified patent and that said Letters Patent is hereby corrected as shown below:

Title page, item (56):U.S. PATENT DOCUMENTS: Delete " 3,536,360 " and substitute -- 3,535,360 --

Col. 8, line 7   Delete " isocyanante " and substitute -- isocyanate

Col. 8, line 9   After " claim " insert -- 1 --

Signed and Sealed this

Thirtieth Day of August, 1994

Attest:

BRUCE LEHMAN

*Attesting Officer*   *Commissioner of Patents and Trademarks*